United States Patent [19]

Quimby

[11] 4,251,661

[45] Feb. 17, 1981

[54] PREPARATION OF 2-TRIFLUOROMETHYL CINCHONINIC ACIDS

[75] Inventor: Daniel J. Quimby, Mt. Holly, N.J.

[73] Assignee: Union Carbide Corporation, New York, N.Y.

[21] Appl. No.: 79,201

[22] Filed: Sep. 26, 1979

[51] Int. Cl.³ .............................................. C07D 215/50
[52] U.S. Cl. ...................................................... 546/170
[58] Field of Search ......................................... 546/170

[56] References Cited

U.S. PATENT DOCUMENTS

| 1,181,485 | 5/1916 | Schwabe | 546/170 |
|---|---|---|---|
| 1,197,462 | 9/1910 | Dohrn | 546/170 |
| 1,816,003 | 7/1931 | Busch | 546/170 |
| 2,220,086 | 11/1940 | Dohrn et al. | 546/170 |
| 2,579,420 | 12/1951 | Coles | 546/170 |
| 3,574,840 | 4/1971 | Riviere et al. | 546/170 |
| 4,009,020 | 2/1977 | Starke et al. | 71/76 |

OTHER PUBLICATIONS

Pinder et al; J. Med. Chem. vol. 11, pp. 267–269 (1968).

*Primary Examiner*—Mary C. Lee
*Attorney, Agent, or Firm*—John S. Piscitello; Dale Lynn Carlson

[57] ABSTRACT

2-Trifluoromethyl cinchoninic acids can be prepared by reaction of an alkali metal 2-aminophenylglyoxylate and 1,1,1-trifluoroacetone in a neutral or acid medium. Preferably reaction is effected by first hydrolyzing isatin, or a substituted isatin, in the presence of an alkali metal hydroxide to produce the alkali metal 2-aminophenylglyoxylate, and then reacting this intermediate product with 1,1,1-trifluoroacetone without isolating it from the reaction medium.

18 Claims, No Drawings

PREPARATION OF 2-TRIFLUOROMETHYL CINCHONINIC ACIDS

FIELD OF THE INVENTION

This invention relates to a novel method of preparing 2-trifluoromethyl cinchoninic acids.

BACKGROUND OF THE INVENTION

2-Trifluoromethyl cinchoninic acid, and substituted 2-trifluoromethyl cinchoninic acids, are known plant growth regulating materials. Such compounds can be prepared, as disclosed by B. M. Pinder and A. Burger (J. Med. Chem, 11, pp 267–269 (1968), by condensation of aniline, or a substituted aniline, with ethyl 4,4,4-trifluoroacetoacetate in the presence of polyphosphoric acid to produce a 2-trifluoromethyl-4-hydroxyquinoline from which the desired 2-trifluoromethyl cinchoninic acid can be obtained by two alternative procedures. In the first of such procedures, the 2-trifluoromethyl-4-hydroxyquinoline is brominated with phosphorus oxybromide to produce the corresponding 2-trifluoromethyl-4-bromoquinoline which is then reacted with n-butyllithium to produce a lithioquinoline which can in turn be treated with dry carbon dioxide to produce the desired 2-trifluoromethyl cinchoninic acid. In the second of such procedures, the 2-trifluoromethyl-4-hydroxyquinoline is chlorinated with phosphorus oxychloride and the resulting 2-trifluoromethyl-4-chloroquinoline is reacted with cuprous cyanide in N-methylpyrrolidone to convert it to the corresponding nitrile which is then hydrolyzed to the desired 2-trifluoromethyl cinchoninic acid. However, not only are both these procedures complex and involved, but they involve the use of corrosive materials such as phosphorus oxybromide and phosphorus oxychloride as well as air- and water-sensitive materials such as butyllithium and copper cyanide.

2-Methylcinchoninic acid has been prepared, as disclosed in Bull. Soc. Chem., France, 1956, 1294, by the reaction of isatin and acetone in 30 percent aqueous potassium hydroxide solution. However, it has been found that when isatin is reacted with 1,1,1-trifluoroacetone in an attempt to produce 2-trifluoromethyl cinchoninic acid in an analogous manner, the desired product cannot be obtained.

SUMMARY OF THE INVENTION

In accordance with the present invention, it has been discovered that 2-trifluoromethyl cinchoninic acids can be prepared in high yields by reaction of an alkali metal 2-aminophenylglyoxylate and 1,1,1-trifluoroacetone in a neutral or acid medium, i.e., at a pH of 7 or below.

Preferably reaction is effected by first hydrolyzing isatin, or a substituted isatin, in the presence of an alkali metal hydroxide to produce the alkali metal 2-aminophenygloxylate, and then reacting this intermediate hydrolysis product with 1,1,1-trifluoroacetone without isolating it from the reaction medium. The overall reaction can be illustrated by the following equation:

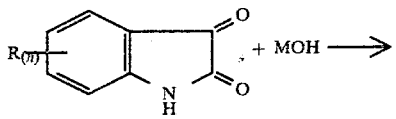+ MOH ⟶

-continued

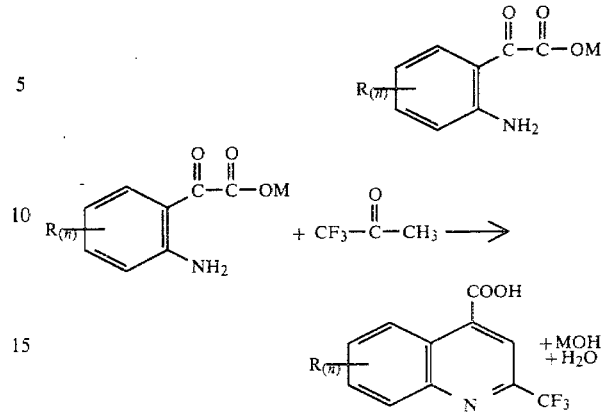

wherein R is selected from the group consisting of halogen, alkyl, aryl and alkoxy radicals, n is an integer having a value of from 0 to 2, and M is an alkali metal.

DETAILED DESCRIPTION

The isatin compounds which can be hydrolyzed to produce the alkali metal 2-aminophenylglyoxylates which are reacted with 1,1,1-trifluoroacetone in accordance with the present invention can be illustrated by the formula:

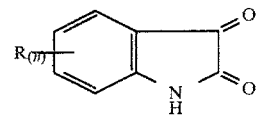

wherein R is selected from the group consisting of halogen, alkyl, aryl and alkoxy radicals, and n is an integer having a value of from 0 to 2. Preferably n is 0, i.e., an unsubstituted isatin is employed. When n is 1 or more, however, each R group present may be the same or different. When R is alkyl, aryl or alkoxy, it preferably contains from 1 to 6 carbon atoms; and when it is halogen, it is preferably chlorine. Typical substituted isatins include 5-methylisatin, 7-methylisatin, 5,7-dimethylisatin, 5-chloroisatin, 7-chloroisatin, 5,7-dichloroisatin, 5-methoxyisatin, 7-methoxyisatin, and 5,7-dimethoxyisatin. Such compounds are well known and can be prepared by direct substitution of isatin or by synthesis from para- or ortho, para-substituted anilines.

Hydrolysis of isatin, or a substituted isatin, to produce an alkali metal 2-aminophenylglyoxylate can be effected by simply dissolving the isatin compound in an aqueous solution containing at least one molar equivalent of an alkali metal hydroxide. An excess of the hydroxide, up to about a three molar excess, or higher, can be employed, if desired, to increase the rate of reaction. However, little advantage is obtained in employing more than a one molar excess of hydroxide. If desired, the solution can be heated to facilitate dissolution of the isatin compound. Other solvents, such as an alcohol, may be added to the solution if desired.

The alkali metal 2-aminophenylglyoxylate produced by hydrolysis of the isatin compound can be illustrated by the formula:

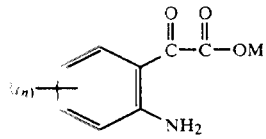

wherein R, n and M are as above defined.

If desired, the alkali metal 2-aminophenylglyoxylate produced by the hydrolysis of isatin, or a substituted isatin, can be isolated from the reaction mixture before it is reacted with 1,1,1,-trifluoroacetone. However, isolation is unnecessary and it is preferred to react these two materials in the same aqueous solution employed to hydrolyze the isatin compound.

After the alkali metal 2-aminophenylglyoxylate has been prepared (whether or not it has been isolated), it is reacted with 1,1,1,-trifluoroacetone in a neutral or acid medium, i.e., at a pH of 7 or below. If desired, an excess of 1,1,1,-trifluoroacetone can be employed, although good results are obtained when equimolar amounts of the reactants are employed. It is believed that the acid acts to promote condensation of the 1,1,1,-trifluoroacetone with the amino group of the 2-aminophenylglyoxylate compound. It has been unexpectedly discovered, however, that ring closure of the intermediate reaction product then follows despite the low pH of the system.

The acid employed to neutralize or acidify the reaction medium must, of course, be soluble in such medium. Such acid should be employed in an amount sufficient to lower the pH of the reaction mixture to 7 or less. The strong material acids, i.e., nitric acid, sulfuric acid, and hydrochloric acid, are preferred.

In addition to an acid, it is desirable to employ a buffer in the reaction mixture in order to maintain the pH of the mixture at the desired level, i.e., at 7 or below. Generally molar ratios of buffer to acid of from 1:10 to from 10:1 are suitable for this purpose. The buffer employed must, of course, be soluble in the reaction mixture.

Most conveniently, reaction between the alkali metal 2-aminophenylglyoxylate and 1,1,1,-trifluoroacetone is effected in the same reaction mixture in which the 2-aminophenylglyoxylate is produced from isatin, i.e., in an aqueous medium. However, if desired, any other inert liquid solvent can be employed. By an inert liquid solvent is meant a solvent which is nonreactive under the conditions of the reaction. Among such solvents are glacial acetic acid, dimethylformamide, dimethylsulfoxide, and alcohols such as methanol, ethanol, propanol, isopropanol, butanol, ethylene glycol, propylene glycol, and the like. In general, an amount of solvent ranging from about 1 to about 100 times, preferably from about 1 to about 10 times, the weight of the reactants can be effectively employed.

Reaction between the alkali metal 2-aminophenylglyoxylate and 1,1,1,-trifluoroacetone can be readily effected at temperatures between about 25° C. and 100° C., preferably between 50° C. and 75° C. However, higher or lower temperatures can be employed if desired.

Atmospheric pressure is usually employed in effecting reaction according to the process of the instant invention. However, pressures both above and below atmospheric pressure can also be employed whenever it is desirable to do so.

The following examples are set forth for purposes of illustration so that those skilled in the art may better understand the invention, and it should be understood that they are not to be construed as limiting this invention in any manner.

EXAMPLE 1

Preparation Of 2-Trifluoromethyl Cinchoninic Acid 3.99 Grams of isatin (0.027 mol) and 5.05 grams of 30% aqueous potassium hydroxide (0.027 mol) were dissolved in 20 mL of water. The solution was then neutralized to a pH of 7 with 10% hydrochloric acid, and buffered with 5 mL of a buffer solution containing 0.96 g of potassium dihydrogen phosphate ($KH_2PO_4$) and 5.72 g of disodium hydrogen phosphate ($Na_2HPO_4$) dissolved in 200 mL of water. Six grams (6 g) of trifluoroacetone (0.054 mol) were then added over a period of 15 hours while the temperature was maintained at about 50° C. The temperature was then raised to about 75° C. and the mixture was heated at that temperature for an additional 20 hours. At the end of this time, the mixture was diluted to twice its volume with water and acidified with 10% hydrochloric acid until 2-trifluoromethyl cinchoninic acid precipitated from the mixture. The product was recovered by filtration and recrystallized from a mixture of water and ethanol. After drying in air, about 2.33 grams of product was recovered, representing a yield of 35.8 percent based on isatin.

Upon standing for several hours, 2.4 grams of isatin also precipitated from the reaction mixture and was recovered by filtration.

What is claimed is:

1. A method of preparing 2-trifluoromethyl cinchoninic acids of the formula:

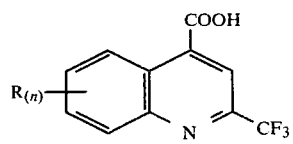

wherein R is selected from the group consisting of halogen, alkyl, aryl and alkoxy radicals, and n is an integer having a value of from 0 to 2, which comprises reacting an alkali metal 2-aminophenylglyoxylate of the formula:

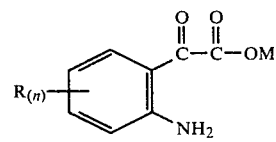

wherein M is an alkali metal, and R and n are as above defined, with 1,1,1,-trifluoroacetone at a pH of no greater than 7.

2. A method as in claim 1 wherein the pH is obtained by means of a strong mineral acid.

3. A method as in claim 1 or 2 wherein the alkali metal 2-aminophenylglyoxylate is potassium 2-aminophenylglyoxylate.

4. A method as in claim 1 wherein n is 0.

5. A method as in claim 4 wherein the pH is obtained by means of a strong mineral acid.

6. A method as in claim 4 or 5 wherein the alkali metal 2-aminophenylglyoxylate is potassium 2-aminophenylglyoxylate.

7. A method as in claim 1 wherein n has a value of from 1 to 2 and R contains from 1 to 6 carbon atoms when it is an alkyl, aryl or alkoxy group, and is chlorine when it is a halogen group.

8. A method as in claim 7 wherein the pH is obtained by means of a strong mineral acid.

9. A method as in claim 7 or 8 wherein the alkali metal 2-aminophenylglyoxylate is potassium 2-aminophenoxylate.

10. A method of preparing 2-trifluoromethyl cinchoninic acids of the formula:

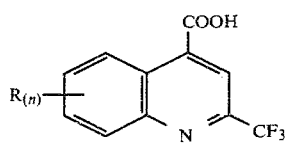

wherein R is selected from the group consisting of halogen, alkyl, aryl and alkoxy radicals, and n is an integer having a value of from 0 to 2, which comprises hydrolyzing an isatin compound of the formula:

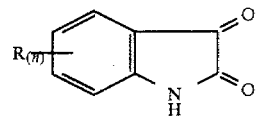

wherein R and n are as above defined, in the presence of an alkali metal hydroxide, and then reacting the hydrolysis product with 1,1,1,-trifluoroacetone at a pH of no greater than 7.

11. A method as in claim 10 wherein the pH is obtained by means of a strong mineral acid.

12. A method as in claim 10 or 11 wherein the alkali metal hydroxide is potassium hydroxide.

13. A method as in claim 10 wherein n is 0.

14. A method as in claim 13 wherein the pH is obtained by means of a strong acid.

15. A method as in claim 13 or 14 wherein the alkali metal hydroxide is potassium hydroxide.

16. A method as in claim 10 wherein n has a value of from 1 to 2 and R contains from 1 to 6 carbon atoms when it is an alkyl, aryl or alkoxy group, and is chlorine when it is a halogen group.

17. A method as in claim 16 wherein the pH is obtained by means of a strong acid.

18. A method as in claim 16 or 17 wherein the alkali metal hydroxide is potassium hydroxide.

* * * * *